United States Patent
Kennefick, III

[19]

[11] Patent Number: 5,976,145
[45] Date of Patent: Nov. 2, 1999

[54] CALCAR MILLING GUIDE AND SYSTEM

[75] Inventor: William H. Kennefick, III, Mansfield, Mass.

[73] Assignee: Johnson & Johnson Professional, Inc., Rayham, Mass.

[21] Appl. No.: 09/088,400

[22] Filed: Jun. 1, 1998

[51] Int. Cl.[6] ................................................. A61B 17/17
[52] U.S. Cl. ............................................. 606/80; 606/86
[58] Field of Search ................................. 606/78, 80, 83, 606/85, 86, 87, 88, 96

[56] References Cited

U.S. PATENT DOCUMENTS

| | | | |
|---|---|---|---|
| 4,777,942 | 10/1988 | Frey et al. | 128/92 |
| 5,403,320 | 4/1995 | Luman et al. | 606/89 |
| 5,540,694 | 7/1996 | DeCarlo et al. | 606/80 |
| 5,643,271 | 7/1997 | Sederholm et al. | 606/80 |
| 5,658,292 | 8/1997 | Axelson, Jr. | 606/86 |
| 5,669,915 | 9/1997 | Caspar et al. | 606/96 |
| 5,688,283 | 11/1997 | Knapp | 606/96 |
| 5,725,596 | 3/1998 | Burke | 623/23 |

*Primary Examiner*—Michael Buiz
*Assistant Examiner*—Tina T. D. Pham
*Attorney, Agent, or Firm*—Nutter, McClennen & Fish, LLP

[57] ABSTRACT

A surgical milling and guide system for use with hip prosthesis trial components includes a mounting member and a guide member which are spaced apart in adjustable increments. The guide member include a milling assembly which is rotatably and slidably translatable with respect to the mounting member. The system further includes a mounting rod for attachment to a femoral proximal sleeve. Various adjustment options are possible for the device to conform to different size prosthetic components such as the proximal sleeve.

14 Claims, 6 Drawing Sheets

CALCAR MILLING GUIDE AND SYSTEM

CROSS-REFERENCE TO RELATED APPLICATIONS

Not applicable.

STATEMENTS REGARDING FEDERALLY SPONSORED RESEARCH

Not applicable.

FIELD OF THE INVENTION

The invention relates to a guide and milling instrument system that is useful to prepare a patient's bone to accept a prosthesis.

BACKGROUND OF THE INVENTION

Replacement of joints, such as knees and hips, with prostheses in human beings has become quite common. A typical hip prosthesis includes a femoral portion or component which is implanted in the femur and an acetabular component which is attached to the pelvis. The femoral component includes a head, which rotates in a socket formed in the acetabular component, and a stem portion which resides in the proximal end of the femur.

To prepare a patient to receive a hip prosthesis, a portion of the proximal end of the femur is first removed. To aid the surgeon in properly aligning the prosthesis, trial prosthetic components are first implanted so that the surgeon can test for the proper alignment and orientation of the prosthesis. Typically, after the trial component is properly positioned, the calcar region of the proximal end of the femur is milled or planed. Once the proper size and fit is evaluated using trial components, the trial components are removed and the actual prosthetic components are implanted.

The milling or planing of the calcar region can be an important step in ensuring a proper fit of the femoral component implant. Due to anatomical variations between individuals and different sizes of prosthetic components, the surgeon must take extreme care in preparing the calcar region so that the prosthetic components are properly aligned and oriented.

In some instances, the trial prosthetic components can interfere with the milling or planing of the calcar region. In fact, the milling or planing can even damage portions of the trial prosthetic components, thereby preventing their re-use.

Accordingly, there remains a need for a surgical system which can properly prepare the proximal end of the femur to receive the femoral component of a hip joint prosthesis for a variety of patients.

BRIEF SUMMARY OF THE INVENTION

The invention is an easily adjustable milling instrument and guide assembly system that enables a surgeon to accurately prepare the proximal end of the femur to receive the femoral component of a hip joint prosthesis. The device includes a mounting member having a longitudinal axis and proximal and distal ends with a bore extending at least partially into the distal end of the mounting member. The mounting member has a mounting frame extending from the mounting member in a direction generally transverse to the longitudinal axis of the mounting member.

The device further includes a guide member which is mountable to the mounting frame. The guide member has a longitudinal axis, proximal and distal ends, and further includes a shaft having a bore extending therethrough. A milling assembly is rotatably mounted within the bore of the shaft. The milling assembly is in the form of an elongate shaft with an end mill cutter at a distal end thereof and a connector element at a proximal end thereof.

A connection frame is mounted to the guide member and extends in a direction generally transverse to the longitudinal axis of the guide member. A connection mechanism mating the connection frame to the mating frame such that the longitudinal axes of the mounting member and the guide member are spaced apart by a desired distance. The connection mechanism allows for the incremental adjustment of distance between the mounting member and the guide member. The system further includes a handle member selectively matable to the system.

The bore at the proximal end of the mounting member is adapted to mate with a mounting rod that is attachable to a portion of a prosthesis trial, such as a hip stem prosthesis trial. Preferably, the bore of the mounting member engages a shaft of the mounting rod, thus enabling the mounting member to be joined to the mounting rod such that the mounting member is able to move vertically with respect to the mounting rod and to pivot about the mounting rod. When the system is properly positioned, a drill is connected to the connector element of the shaft. Upon actuation of the drill, the shaft and end mill cutter rotate and mill or plane the proximal end of the femur in the calcar region of the femur.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
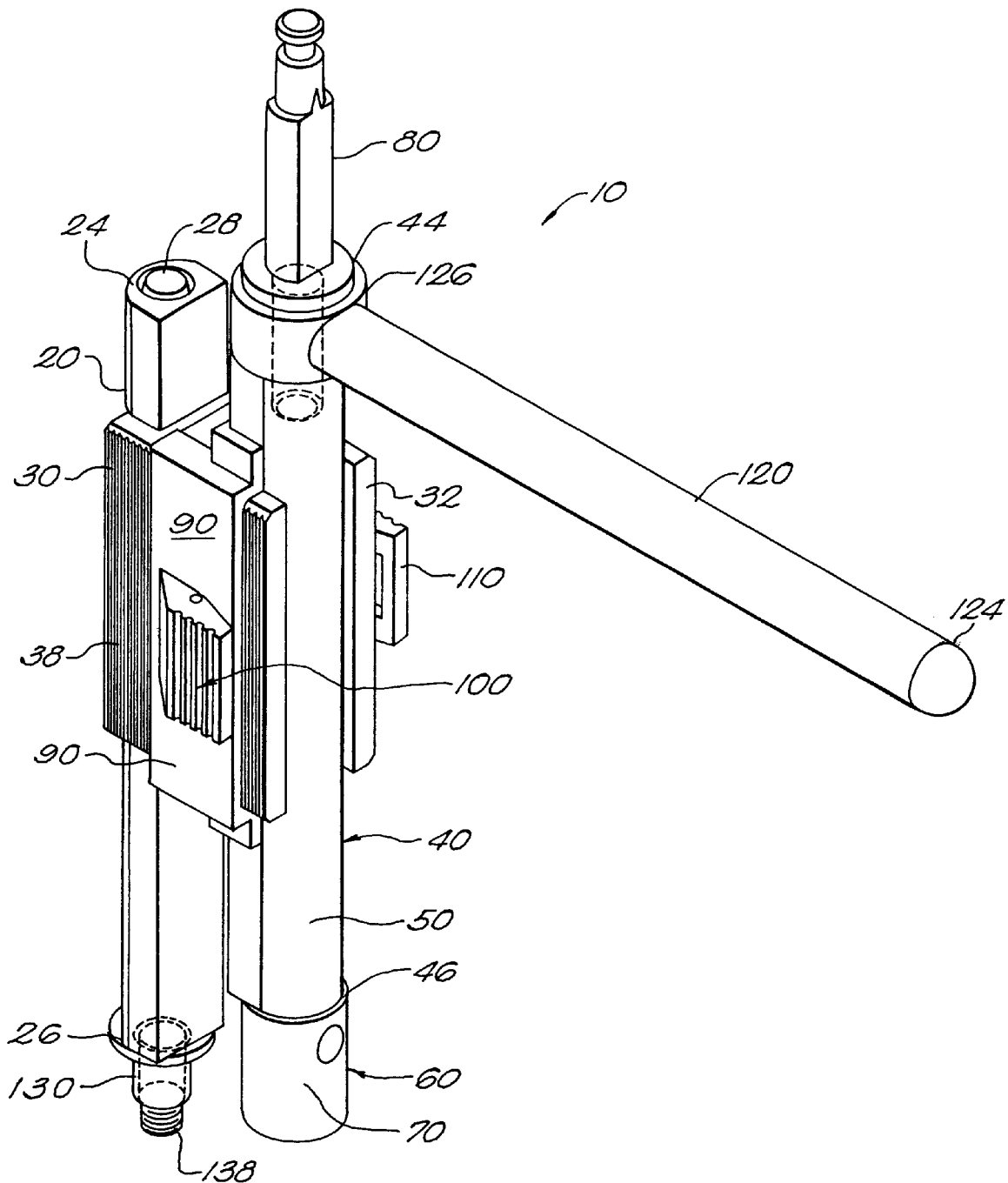
FIG. 1 is a perspective view of a calcar milling guide and system constructed according to the present invention.

Referring to FIG. 1, a surgical milling and guide device 10 for use in preparing a proximal end of a femur to accept a femoral component of a hip prosthesis is shown. Generally, the milling and guide device 10 includes a mounting member 20, a mounting frame 30, a guide member 40, a milling assembly 60, a connection frame 90, a connection mechanism 100, and a handle member 120.

Figure 2:
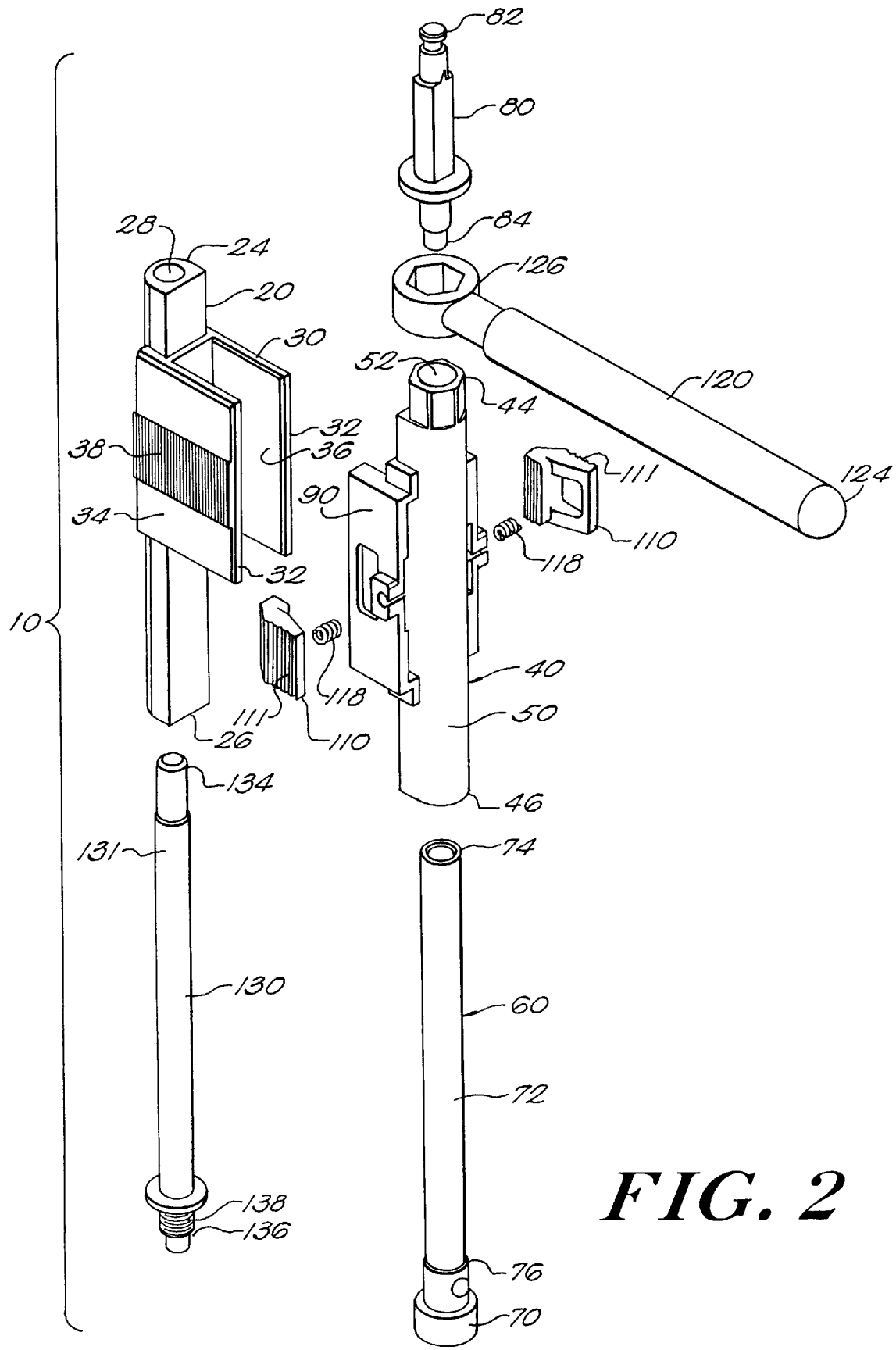
FIG. 2 is an exploded view of the system shown in FIG. 1.
Figure 3:
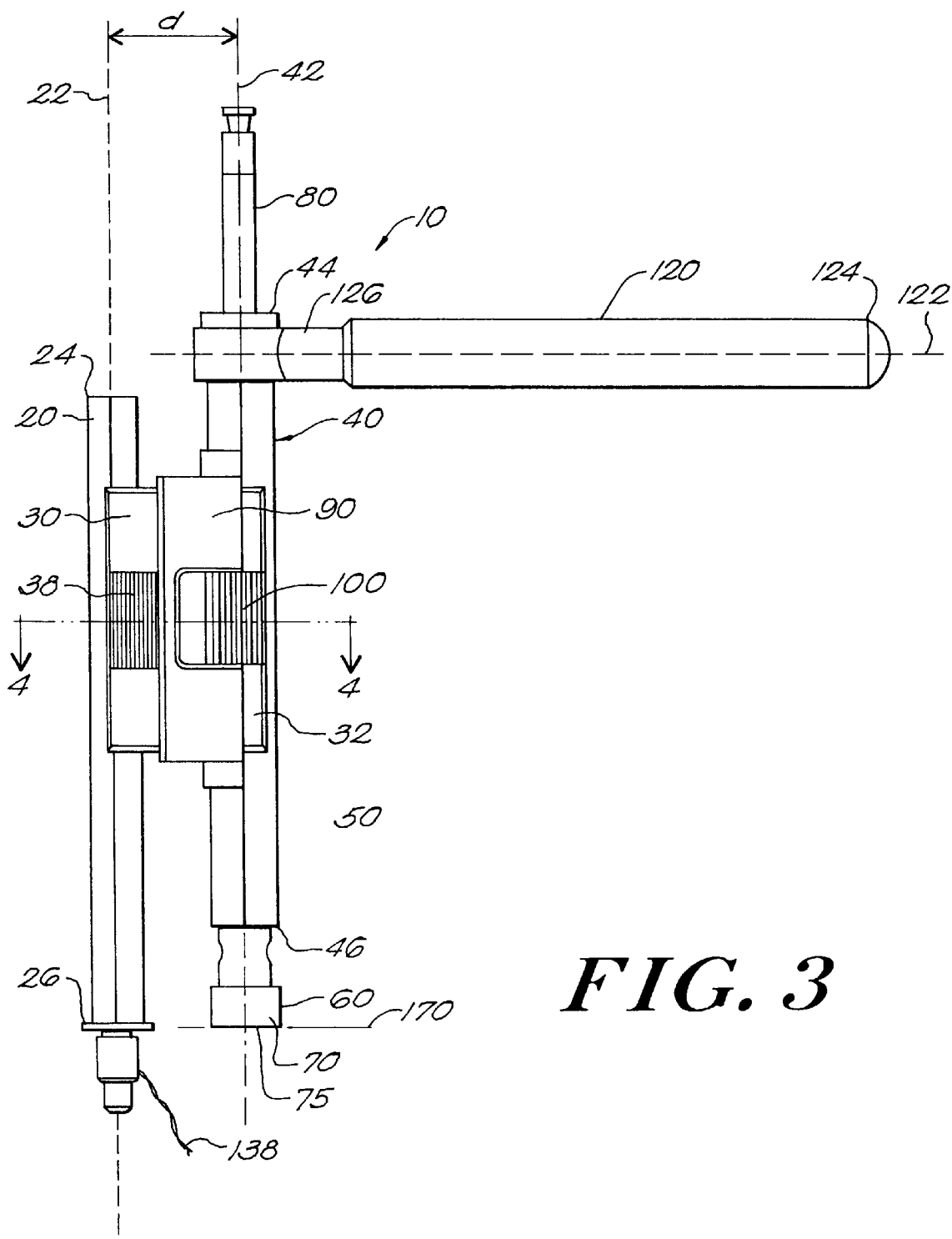
FIG. 3 is a side view of the milling system of FIG. 1.
Figure 4:
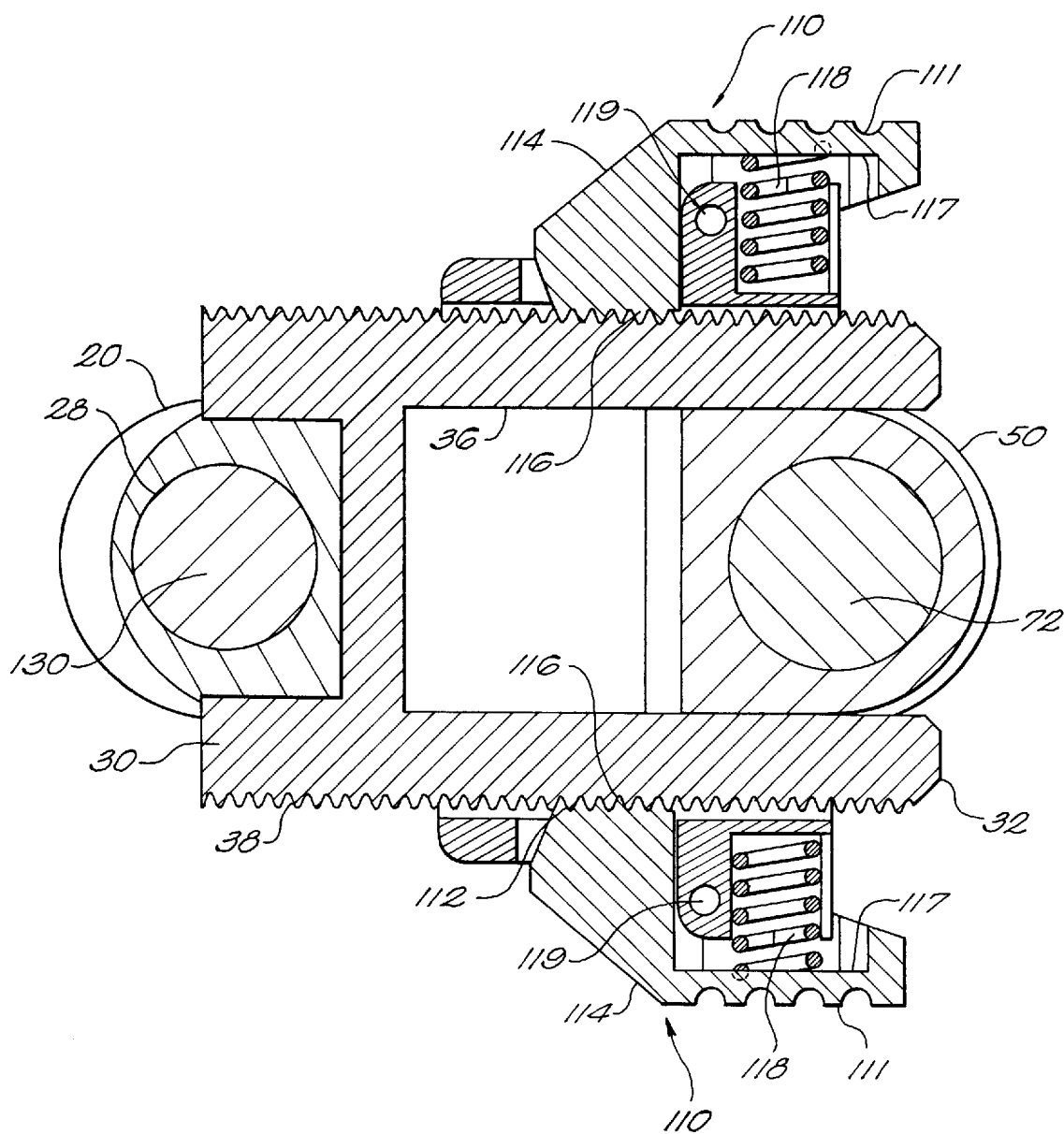
FIG. 4 is a sectional view taken along line 4—4 in FIG. 3.
Figure 5:
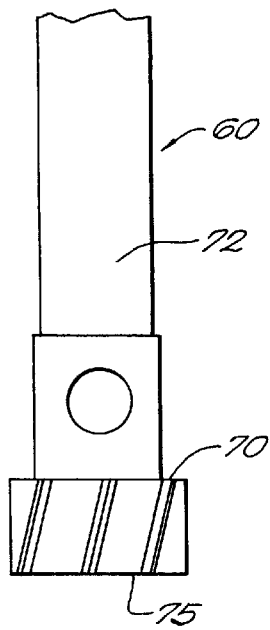
FIG. 5 is a side view of one embodiment of an end mill cutter useful with the present invention.
Figure 6:
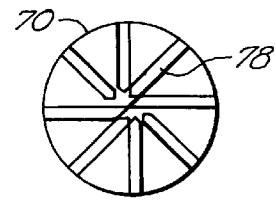
FIG. 6 is an end view of the end mill cutter of FIG. 5.
Figure 8:
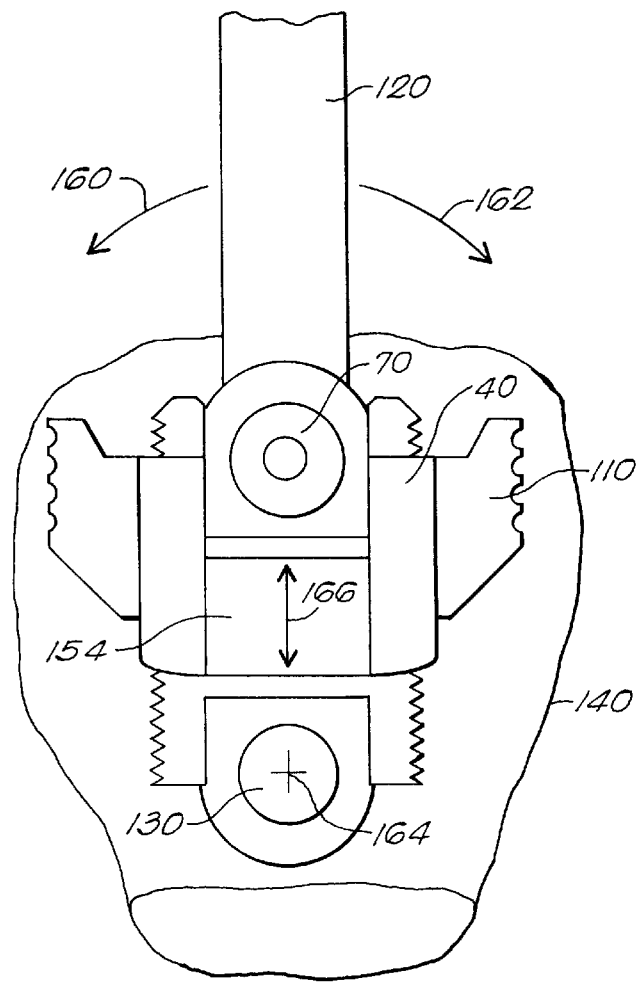
FIG. 8 illustrates certain adjustment variations for the milling guide of the invention.

The mounting member 20, as illustrated in FIGS. 1–3, has a longitudinal axis 22, a proximal end 24 and a distal end 26. The mounting member 20 further includes a bore 28 extending at least partially into the distal end 26 of the mounting member 20. Although the bore 28 is shown to be of a circular shape, one of ordinary skill in the art will appreciate that it can be of any other suitable shape that allows a sufficient amount of pivoting or rotation of the mounting member 20, when the mounting member 20 is mounted to a mounting rod 130, as described below.

The mounting member 20 includes a mounting frame 30 which extends from the mounting member 20 in a direction generally transverse to the longitudinal axis 22 of the mounting member 20. The mounting frame 30 has two protruding flange portions 32, each having a superior mating surface 34 and an inferior surface 36. The superior mating surface 34 has a plurality of detents 38 formed thereon which extend in a direction generally parallel to the longitudinal axis 22 of the mounting member 20. The detents 38 may extend across the entire length of the superior mating surface 34 or they may extend only partially across the superior mating surface 34. The detents 38 engage the connection mechanism 100 of the device 10 to provide for the incremental adjustment of the guide member 40 relative to the mounting member 20, as discussed below.

The guide member 40 has a longitudinal axis 42, a proximal end 44 and a distal end 46. The guide member 40 includes a shaft portion 50 having a bore 52 extending therethrough, through which is mounted a milling assembly 60 for the milling of the proximal end of the femur.

The milling assembly 60 is rotatably mounted within the bore 52 of the shaft 50. As shown in FIGS. 2, 3, 5 and 6, the milling assembly 60 further includes an end mill cutter 70 with cutting teeth 78 at a distal end thereof. The milling assembly 60 further includes an elongate shaft 72 which extends proximally from the end mill cutter 70 and has a proximal end 74 and a distal end 76. The elongate shaft 72 is rotatably mountable within the bore 52 of the guide member 40. A proximal end 74 of the elongate shaft 72 is attachable to a connector element 80. In an exemplary embodiment, the connector element 80 of the milling assembly 60 is a Hudson end separately attachable at a first end 82 to a drill (not shown) and at a second end 84 to the proximal end 74 of the elongate shaft 72.

End mill cutters suitable for use in a surgical environment to mill or plane a bone can be used with the system of the invention. In one embodiment, however, the end mill cutter 70 has the following characteristics: 8 cutting teeth, 10° RH Helix/RH Cut, cylindrical land with end cutting teeth, 7° primary, 15° secondary, and 2 center cutting flutes.

The guide member 40 further includes a connection frame 90 which extends in a direction generally transverse to the longitudinal axis 42 of the guide member 40. The connection frame 90 may be formed of spaced elements positioned on opposing sides of the guide member shaft portion 50 that receive the extending flange portions 32 of the mounting frame 30. The connection frame 90 further includes connection mechanism 100 which secures the guide member 40 to the mounting member 20. The connection mechanism 100 also enables the incremental adjustment of the guide member 40 relative to the mounting member 20 such that the longitudinal axis 22 of the mounting member 20 and the longitudinal axis 42 of the guide member 40 are spaced apart by a desired distance "d", as shown in FIG. 3. The distance "d" can be adjusted as needed, within the range of about 2.5 cm to 5 cm. The connection mechanism 100 further includes at least one pawl member 110 mounted on the connection frame 90 on the guide member 40.

As shown in FIGS. 1–4, the connection mechanism also includes a pawl member 110 that engages and interlocks with the detents 38 of the mounting frame 30. In the illustrated embodiment, pawls 110 are positioned on either side of the connection frame 90.

Each pawl member 110 has a tab portion 111, a superior surface 114 and an inferior engaging surface 116. The inferior engaging surface 116 has a plurality of pawl teeth 112 which are adapted to engage and interlock with the detents 38 formed on the mounting frame 30. In such an interlocking engagement, the at least one pawl member 110 secures the guide member 40 to the mounting member 20 while allowing for the selective incremental adjustment of the distance (d) between the longitudinal axis 22 of the mounting member 20 and the longitudinal axis 42 of the guide member 40. The pawl member 110 may be secured to the connection frame 90 of the guide member 40 by a securing pin 119.

The connection mechanism 100 further includes a spring 118 disposed within a recess 117 formed beneath the pawl tab portion 111 and biased against the connection frame 90 to facilitate adjustment of the guide member 40 relative to the mounting member 20. The spring 118, when in an extended position between the at least one pawl member 110 and the connection frame 90, biases the pawl 110 to a position in which the pawl teeth 112 engage detents 38 of mounting frame 30, thereby preventing unintentional disengagement of the pawl teeth 112 from the detents 38. Incremental adjustment of the device 10 may be made by grasping and depressing the pawl tab 111 to remove the engagement between detents 38 and pawl teeth 112. Once this engagement is removed, the guide member 40 may be moved in a direction generally transverse to the longitudinal axis 22 of the mounting member 20. Releasing the pawl tab 111 re-engages the pawl teeth 112 to the detents 38 and secures the guide member 40 to the mounting member 20 in the desired position.

The system further includes a handle member 120 which extends in a direction generally transverse to the longitudinal axis 42 of the guide member 40. The handle 120 allows a surgeon to grasp and manipulate the system from a variety of positions depending on factors such as the location of the incision made on a patient. The handle 120 has a longitudinal axis 122, a proximal end 124 and a distal end 126. The distal end 126 of the handle 120 includes a hexagonally shaped coupling 128 which is attachable to a complementarily shaped proximal end 44 of guide member 40. A person of ordinary skill in the art will appreciate that differently shaped surfaces may be used for the interlocking handle and guide member as necessary to achieve the purpose of the invention. The handle 120 may also be used to rotate or pivot the milling assembly 60 to provide a radial cutting path when the system is mounted on a mounting rod 130.

Figure 7:
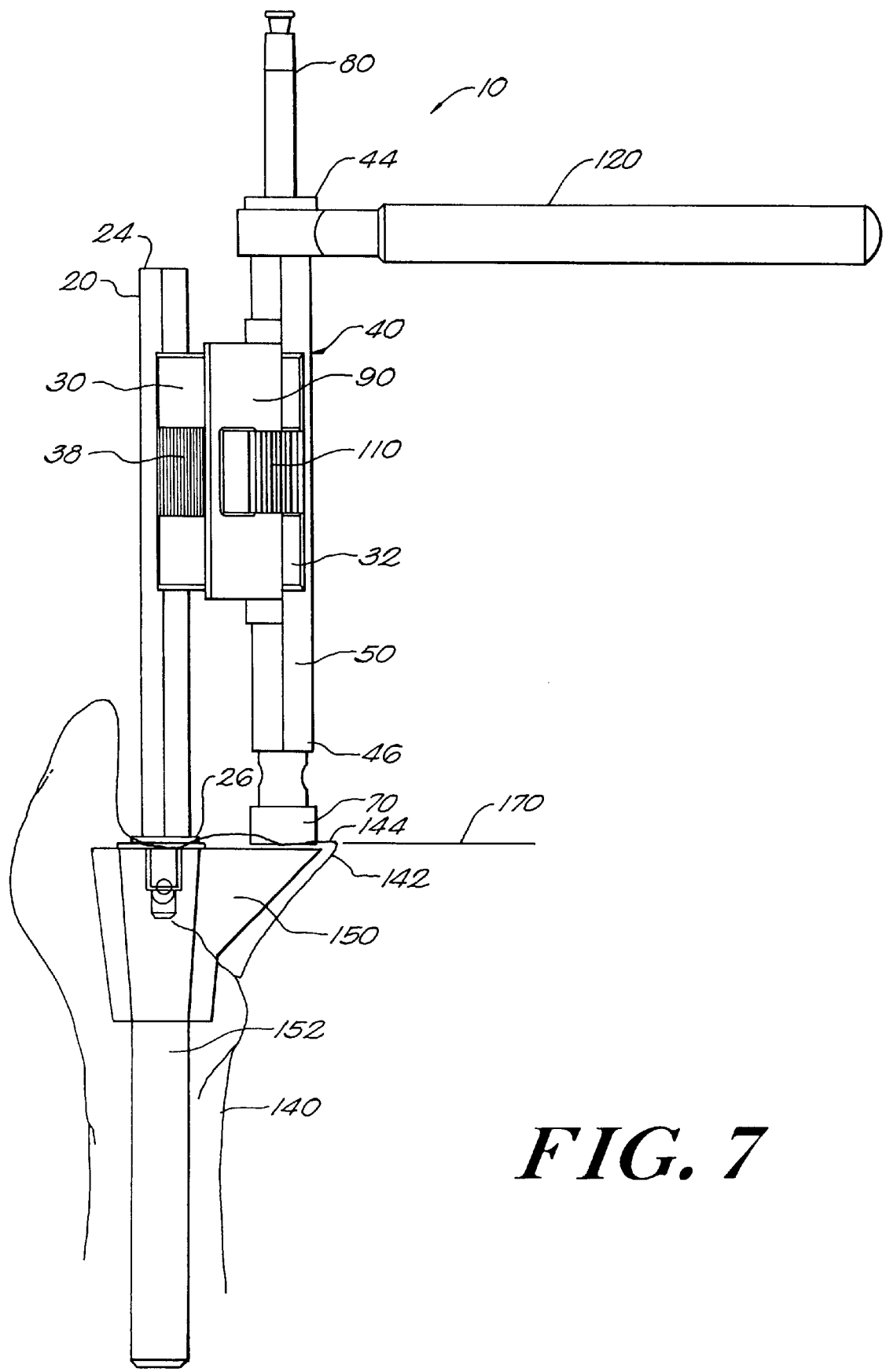
FIG. 7 is side view of the system of the present invention when attached to a prosthesis trial component disposed within a femur.

As noted above and as illustrated in FIGS. 1–3 and 7, the system also includes a mounting rod 130, having a proximal end 134 and a distal end 136. The mounting rod 130 further includes a threaded portion 138 proximate the distal end 136. The threaded portion 138 is matable with a trial component such as a proximal portion of a hip stem trial component 150, as shown in FIG. 7. Once the mounting rod 130 is attached to the proximal sleeve 150, the system 10 is secured to the mounting rod 130 by positioning the shaft 131 of the mounting rod 130 within the bore 28 of the mounting member 20. As so mated, the system 10 is able to move vertically with respect to the mounting rod 130, and the system 10 is able to rotate or pivot about the mounting rod 130.

In an exemplary embodiment, the milling guide and system as described herein may be further assembled as follows. First, the mounting rod 130 is screwed onto a proximal portion 150 of a trial femoral implant for a hip prosthesis. The handle 120, in its desired orientation, is then fitted onto the proximal end 44 of the guide member 40. Next, the milling assembly 60 is inserted into the bore 52 of the guide member shaft 52 and secured proximate the proximal end 44 of the guide member 40 by connector element 80. The guide member 40 is then joined to the mounting member 20 by interlocking engagement of the connection mechanism 100 on the guide member 40 to the mounting frame 30 on the mounting member 20, as described above. Thereafter, the mounting member 20, to which is attached the guide member 40, is positioned on the mounting rod 130. As assembled, the distal end 26 of the mounting member 20 and the bottom portion 75 of the end mill cutter 70 are substantially flush with one another on a calcar plane 170, as shown in FIGS. 3 and 7. The calcar region 144 of the proximal femur 142 is now ready to be milled using the system 10.

As noted above, the milling system of the invention enables the adjustment of the distance (d) between axes 22, 42. Once the system has been assembled as described above, the position of the guide member 70 is adjustable relative to the position of the mounting member 20 to thereby effect a corresponding variation in the position of the end mill cutter 70. The guide member 70 is adjustable in the medial/lateral direction, as designated by arrow 166 in the range of about 2.5 cm to 5 cm. By virtue of the rotatable mounting of the mounting member 20 to the mounting rod 130, the guide member 40, when attached to the mounting member 20, can be pivotally adjusted in a radial cutting path about a center axis 164 of the mounting rod 130. By grasping the handle 120, the surgeon can move the end mill cutter 70 in the radial cutting path, as illustrated by arrows 160 and 162, with respect to the center axis 164 of the mounting rod 130. Varying the distance (d) between the guide member 40 and the mounting member 20, effectively decreases the effective radial cutting path of the end mill cutter 70.

The surgical device as described herein may be made from a variety of biocompatible materials, such as stainless steel, titanium, anodized aluminum or other similar metals and metal alloys.

The surgical device and system of the present invention may be employed in a variety of surgical applications, particularly those related to hip prostheses, and more particularly to the attachment of a femoral component of a hip prosthesis. An exemplary procedure for using the surgical system of the present invention begins with the step of removing a portion of a proximal end of a femur. A trial femoral stem component 150 and stem body 152 as illustrated in FIG. 7 are then positioned within the proximal end of the femur. The calcar region 144 of the proximal femur 142 is then milled flush to the proximal sleeve 150 using the system as described herein. Milling can be performed in a plunge cut fashion or in a substantially side cutting motion.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A surgical device, comprising:
    a mounting member having a longitudinal axis and proximal and distal ends with a bore extending at least partially into the distal end of the mounting member;
    a mounting frame extending from the mounting member in a direction generally transverse to the longitudinal axis of the mounting member; and
    a guide member, mountable to the mounting frame, having a longitudinal axis, proximal and distal ends, and including;
        a shaft having a bore extending therethrough,
        a milling assembly rotatably mounted within the bore of the shaft, the milling assembly having an end mill cutter at a distal end thereof, an elongate shaft extending proximally from the end mill cutter, and a connector element at a proximal end of the shaft,
        a connection frame extending in a direction generally transverse to the longitudinal axis of the guide member, and adjustably matable to the mounting frame; and
        a connection mechanism effective to securely mate the connection frame to the mounting frame such that the longitudinal axes of the mounting member and the guide member are adjustably spaced apart by a desired distance.

2. The surgical device of claim 1, further comprising a mounting rod having a longitudinal axis and proximal and distal ends, wherein the mounting member is rotatably and slidably mounted on the mounting rod.

3. The surgical device of claim 2, wherein when the guide member is attached to the mounting member, the end mill cutter travels in a radial path about a center axis defined by the longitudinal axis of the mounting rod.

4. The surgical device of claim 2, wherein the distal end of the mounting rod is attachable to a prosthesis trial component.

5. The surgical device of claim 1, wherein the connector element of the milling assembly is a Hudson end separately attachable at a first end to the elongate shaft and at a second end to a drill.

6. The surgical device of claim 1, wherein the mounting member has a plurality of detents formed on the mounting frame, the detents oriented in a direction generally parallel to the longitudinal axis of the mounting member.

7. The surgical device of claim 6, wherein the connection frame includes at least one pawl member having a superior surface and an inferior engaging surface, the inferior engaging surface having a plurality of pawl teeth disposed thereon, the pawl teeth adapted to engage and interlock with the detents formed on the mounting frame.

8. The surgical device of claim 7, wherein the at least one pawl member allows for the selective incremental adjustment of distance between the longitudinal axes of the mounting member and the guide member.

9. The surgical device of claim 8, further comprising a spring disposed between the inferior surface of the at least one pawl member and the connection frame, the spring being effective to bias the pawl teeth into engagement with the detents of the mounting frame.

10. The surgical device of claim 1 further comprising a handle member selectively matable to the system.

11. The surgical device of claim 10, wherein the handle extends from the guide member in a direction generally transverse to the longitudinal axis of the guide member.

12. The surgical device of claim 10, wherein the handle is selectively adjustable to a variety of positions relative to the system.

13. The surgical device of claim 1, wherein the bore of the mounting member extends into the entire length of the mounting member.

14. A surgical system, comprising:

a milling device including:
- a mounting member having a longitudinal axis and proximal and distal ends with a bore extending into the distal end of the mounting member;
- a mounting frame extending from the mounting member;
- a guide member, selectively mountable to the mounting frame, having a longitudinal axis, proximal and distal ends, and including:
  - a shaft having a bore extending therethrough,
  - a milling assembly rotatably mounted within the bore of the shaft, the milling assembly having an end mill cutter at a distal end thereof, an elongate shaft extending proximally from the end mill cutter, and a connector element at a proximal end of the shaft,
  - a connection frame extending from the guide member, and adjustably matable to the mounting frame,
  - a connection mechanism effective to securely mate the connection frame to the mounting frame such that the longitudinal axes of the mounting member and the guide member are adjustably spaced apart by a desired distance; and
- a handle member selectively matable to the device; and a mounting post having a proximal and a distal end, wherein the milling device is rotatably and slidably mounted upon the proximal end of the mounting post.

* * * * *